US010420344B2

(12) United States Patent
Yoshikawa et al.

(10) Patent No.: US 10,420,344 B2
(45) Date of Patent: Sep. 24, 2019

(54) METHOD FOR PRODUCING STABILIZED HYPOBROMOUS ACID COMPOSITION, STABILIZED HYPOBROMOUS ACID COMPOSITION, AND SLIME INHIBITION METHOD FOR SEPARATION MEMBRANE

(71) Applicant: ORGANO CORPORATION, Tokyo (JP)

(72) Inventors: Hiro Yoshikawa, Tokyo (JP); Shintaro Someya, Tokyo (JP); Masato Tsuji, Tokyo (JP); Chiharu Ohmori, Tokyo (JP)

(73) Assignee: ORGANO CORPORATION, Tokyo (JP)

( * ) Notice: Subject to any disclaimer, the term of this patent is extended or adjusted under 35 U.S.C. 154(b) by 374 days.

(21) Appl. No.: 14/912,763

(22) PCT Filed: May 12, 2014

(86) PCT No.: PCT/JP2014/062571
§ 371 (c)(1),
(2) Date: Feb. 18, 2016

(87) PCT Pub. No.: WO2015/029504
PCT Pub. Date: Mar. 5, 2015

(65) Prior Publication Data
US 2016/0198721 A1 Jul. 14, 2016

(30) Foreign Application Priority Data

Aug. 28, 2013 (JP) .................... 2013-176912
Apr. 25, 2014 (JP) .................... 2014-090914

(51) Int. Cl.
*A01N 59/00* (2006.01)
*B01D 65/08* (2006.01)
*C01B 11/20* (2006.01)
*C02F 1/76* (2006.01)
*B01D 65/02* (2006.01)
*B01D 61/04* (2006.01)
*B01D 71/56* (2006.01)
*C02F 1/44* (2006.01)
*B01D 61/02* (2006.01)
*C02F 103/02* (2006.01)

(52) U.S. Cl.
CPC ............. *A01N 59/00* (2013.01); *B01D 61/04* (2013.01); *B01D 65/02* (2013.01); *B01D 65/08* (2013.01); *C01B 11/20* (2013.01); *C02F 1/766* (2013.01); *B01D 61/025* (2013.01); *B01D 71/56* (2013.01); *B01D 2311/04* (2013.01); *B01D 2311/12* (2013.01); *B01D 2321/162* (2013.01); *B01D 2321/168* (2013.01); *C02F 1/441* (2013.01); *C02F 2103/023* (2013.01); *C02F 2303/04* (2013.01); *C02F 2303/16* (2013.01); *C02F 2303/20* (2013.01)

(58) Field of Classification Search
CPC ........ A01N 59/00; B01D 61/04; B01D 65/08; B01D 65/02; B01D 2311/12; B01D 2311/04; B01D 2321/168; B01D 61/025; B01D 2321/162; B01D 71/56; C02F 1/766; C02F 2303/20; C02F 2303/16; C02F 2303/04; C02F 2103/023; C02F 1/441; C01B 11/20
See application file for complete search history.

(56) References Cited

U.S. PATENT DOCUMENTS

| 4,988,444 | A | * | 1/1991 | Applegate ................ A61L 2/18 210/636 |
|---|---|---|---|---|
| 4,992,209 | A | | 2/1991 | Smyk et al. |
| 5,683,654 | A | | 11/1997 | Dallmier et al. |
| 6,015,782 | A | | 1/2000 | Petri et al. |
| 6,037,318 | A | | 3/2000 | Na |
| 6,068,861 | A | | 5/2000 | Moore, Jr. et al. |
| 6,123,870 | A | | 9/2000 | Yang et al. |
| 6,156,229 | A | | 12/2000 | Yang et al. |
| 6,287,473 | B1 | | 9/2001 | Yang et al. |
| 6,303,037 | B1 | | 10/2001 | Tamura et al. |
| 6,423,267 | B1 | | 7/2002 | Yang et al. |
| 6,699,684 | B2 | * | 3/2004 | Ho .......................... C12Q 1/04 435/29 |
| 2002/0110603 | A1 | | 8/2002 | Moore, Jr. et al. |
| 2006/0032823 | A1 | | 2/2006 | Harrison et al. |
| 2006/0051284 | A1 | | 3/2006 | Fishler et al. |
| 2010/0035950 | A1 | | 2/2010 | Sauer et al. |
| 2016/0198721 | A1 | | 7/2016 | Yoshikawa et al. |

FOREIGN PATENT DOCUMENTS

| CN | 102015078 | 4/2011 |
|---|---|---|
| JP | 7-163979 | 6/1995 |

(Continued)

OTHER PUBLICATIONS

Korean Decision of Rejection with English Translation in respect to Korean Application No. 10-2016-7004146, dated Jan. 31, 2018.
(Continued)

*Primary Examiner* — David C Mellon
(74) *Attorney, Agent, or Firm* — Greenblum & Bernstein, P.L.C.

(57) ABSTRACT

Provided is a method for producing a one-liquid stabilized hypobromous acid composition which contains substantially no bromate ions, has excellent sterilization performance, exhibits almost no corrosiveness relative to metals, and displays excellent storage stability. This method for producing the stabilized hypobromous acid composition includes a step in which a reaction is induced by adding, under an inert gas atmosphere, bromine to a mixed solution including water, an alkali hydroxide, and sulfamic acid, wherein the proportion of bromine added is not more than 25 wt % relative to the total weight of the composition.

3 Claims, No Drawings

(56) References Cited

FOREIGN PATENT DOCUMENTS

| | | |
|---|---|---|
| JP | H09-94585 | 4/1997 |
| JP | 9-220449 | 8/1997 |
| JP | 11-501974 | 2/1999 |
| JP | 11-511779 | 10/1999 |
| JP | 2002-516827 | 6/2002 |
| JP | 2002-543048 | 12/2002 |
| JP | 2003-117553 | 4/2003 |
| JP | 2005-537920 | 12/2005 |
| JP | 2006-263510 | 10/2006 |
| JP | 2010-063998 | 3/2010 |
| JP | 2010-515759 | 5/2010 |
| JP | 2011-50843 | 3/2011 |
| JP | 2013-34938 | 2/2013 |
| JP | 2013-169511 | 9/2013 |
| JP | 2013-202481 | 10/2013 |
| JP | 2014-101251 | 6/2014 |
| KR | 1020110007180 | 1/2011 |
| WO | 99/06320 | 2/1999 |
| WO | 99/62339 | 12/1999 |
| WO | 00/64806 | 11/2000 |
| WO | 2009/128328 | 10/2009 |
| WO | 2015/029504 | 3/2015 |

OTHER PUBLICATIONS

Chinese Office Action issued in Counterpart Patent Appl. No., dated Nov. 28, 2016, along with an english translation thereof.
Chinese Third Notice of Grounds for Rejection with English Translation in respect to Chinese Patent Application No. 201480047664.1, dated Dec. 8, 2017.
Office Action issued in China Counterpart Patent Appl. No. 201480047664.1, dated Jun. 13, 2017, along with an english translation thereof.
Korean Search Report issued in Patent Application No. 10-2016-7004146, dated Aug. 4, 2017, with English translation thereof.
Notice of Grounds for Rejection in Japanese Application No. 2012-254118, dated Jan. 12, 2016, along with an english translation thereof.
International Search Report issued in PCT/JP2014/062571, dated Jun. 17, 2014.
International Preliminary Examination Report in PCT/JP2014/062571, dated Mar. 10, 2016.
Singaporean Search Report issued in Patent Application No. 11201601207U, dated Nov. 8, 2016.
Singaporean Search Report issued in Patent Application No. 10201702983P, dated Sep. 7, 2017.
Japanese Notice of Grounds for Rejection in respect to Japanese Application No. 2014-090914, dated Jan. 30, 2018.
Saudi Arabian Notice of Substantive Examination Report with English Translation in respect to Saudi Arabian Application No. 516370626, dated Jan. 8, 2018.
Korean Decision of Rejection with English Translation in respect to Korean Application No. 10-2016-7004146, dated Apr. 11, 2018.
Examination Report issued in corresponding Indian Patent Application No. 201617035564 dated Oct. 11, 2018.
Jane Kucera: Reverse Osmosis, Design Processes, and Applications for Engineers, 2010, Scrivener Publishing, pp. 136, 137, 180, 181, 370, 371.
Official Action dated May 21, 2018 in Indonesian patent application No. P00202602002, and English Translation thereof.
Decision of Rejection in Chinese Patent Application No. 201480047664.1 and English language translation thereof.
Notice of Grounds for Rejection in Korean Patent Application No. 10-2018-7013587, dated Aug. 2, 2018.
Non-final Office Action in co-pending U.S. Appl. No. 15/306,647 dated Sep. 6, 2018.
International Search Report issued in Patent Application No. PCT/JP2015/054269, dated May 19, 2015.
International Preliminary Report on Patentability issued in Patent Application No. PCT/JP2015/054269, dated Nov. 17, 2016.
Japanese Office Action issued in Counterpart Patent Appl. No. 2016-517824, dated Apr. 18, 2017, along with an English Translation.
Korean Office Action with English Translation in respect to Korean Patent Application No. 10-2016-7031143, dated Feb. 12, 2018.
Singapore International Search Report for Singapore Application No. 11201609169U, dated Dec. 13, 2017.
Singapore Written Opinion for Singapore Application No. 11201609169U, dated Dec. 13, 2017.
Japanese Office Action issued in Counterpart Patent Appl. No. 2016-517824, dated Nov. 21, 2017, along with an English translation.
Office Action issued in Korea Patent Application No. 10-2018-7029940, dated Nov. 14, 2018, with English translation.
Office Action in Chinese Patent Application No. 201480047664.1, dated Feb. 2, 2019.
Evidence 1 (cited in 1, above): Application of Reverse Osmosis Water Treatment, Ho-so Cho, Editor, China Electric Power Publications, 2004, p. 118 (in Chinese—discussed in 1, above).
Substantive Examination Adverse Report issued in corresponding Malaysian Patent Application dated Jan. 31, 2019.
Decision of Rejection in Korean Patent Application No. 10-2018-7013587, dated Feb. 7, 2019 and English language translation thereof.
Notice of Allowance in Korean Application No. 10-2018-7013587 dated Mar. 29, 2019 and English language translation thereof.
Translation of allowed claims in Korean Application No. 10-2018-7013587.
California Energy Commission Website (https://www.energy.ca.gov/) as of Mar. 27, 2019.
Notice of Grounds for Rejection dated Apr. 29, 2019 in Korean application No. 01-2019-7007000, and English language translation thereof.
"Standard of Sewerage Facility 2011" (cited in (1), p. 3).
Examination Report in Indian Application No. 201627006011 (in English and non-English) dated Jun. 17, 2019.

* cited by examiner

METHOD FOR PRODUCING STABILIZED HYPOBROMOUS ACID COMPOSITION, STABILIZED HYPOBROMOUS ACID COMPOSITION, AND SLIME INHIBITION METHOD FOR SEPARATION MEMBRANE

TECHNICAL FIELD

The present invention relates to a method for producing a stabilized hypobromous acid composition for controlling biofouling in aqueous systems, and a stabilized hypobromous acid composition.

Further, the present invention also relates to a slime inhibition method for a separation membrane such as an RO membrane.

BACKGROUND ART

Sodium hypochlorite is the most commonly used fungicide for controlling biofouling in aqueous systems including industrial water systems such as water-cooling systems and papermaking processes, but in those cases where superior sterilization performance is required, if the sodium hypochlorite is used in a large amount, then corrosion of the piping and problems of odor may sometimes arise. Accordingly, in these cases, sodium hypobromite is typically used due to its higher level of sterilization performance, but because sodium hypobromite is unstable, techniques in which a bromine compound such as sodium bromide and sodium hypochlorite are mixed together immediately prior to use to generate the sodium hypobromite within the system are typically employed industrially. However, even in these cases, problems including the difficulty of ensuring uniform mixing of the two liquids and corrosion still remain, and therefore a one-liquid stabilized hypobromous acid composition having excellent storage stability is required.

Various oxidizing bromine formulations comprising a bromine stabilizer such as sulfamic acid, bromine, and a hydroxide or the like have been proposed as one-liquid stabilized hypobromous acid compositions.

A technique for activating bromide ions to generate hypobromites by adding a bromine stabilizer and then adding an oxidizing agent such as a hypochlorite has also been proposed. A method using sodium hypochlorite as an oxidizing agent, and then utilizing the hypobromous acid produced upon reaction with a bromine compound is disclosed in Patent Document 1 and Patent Document 2. Patent Document 1 discloses a method of adding sulfamic acid to a premixed solution composed of sodium hypochlorite and a bromine compound, and Patent Document 2 discloses a method of adding a bromine compound to a premixed solution composed of sodium hypochlorite and sulfamic acid. In either case, as the products from the sulfamic acid may decompose, the addition is preferably performed at a temperature of about 10 to 45° C., and is more preferably performed at about 20° C. However, in these methods, chlorine and chloride ions derived from the sodium hypochlorite are retained in the product, meaning problems such as corrosion remain. Further, the hypobromous acid is unstable, and generation of bromic acid as a by-product is problematic.

A method in which reaction is performed using bromic acid as the oxidizing agent instead of a chlorine-based oxidizing agent is disclosed in Example 1 and Example 2 of Patent Document 3. The two equations shown below are disclosed as the reaction mechanism, with the contribution of the bromic acid to the reaction being an essential factor.

However, in terms of safety and the like, the use of bromic acid as a raw material in an industrial setting is problematic.

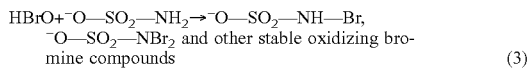

A method of reacting only bromine to obtain an oxidizing bromine-based composition without using an oxidizing agent is disclosed in another embodiment of Example 2 and in Example 3 of Patent Document 3, and in Example 4 of Patent Document 4. However in the other embodiment of Example 2 of Patent Document 3 and Example 4 of Patent Document 4, the corrosiveness is high and a significant problem, and the other embodiment of Example 2 in Patent Document 3 also suffers from problems of a strong irritating odor and poor storage stability. Further, in Example 3 of Patent Document 3, the formation of large amounts of crystals was confirmed, and in terms of generating a large amount of crystals, this method also utilizes the oxidizing power of the bromic acid generated during the reaction, so that the product actually produced by this reaction suffers from a problem of containing significant residual bromic acid.

Moreover, known slime inhibition methods for separation membranes such as RO membranes include methods which use various slime inhibitors. Oxidizing agents such as hypochlorous acid and hypobromous acid are typically representative slime inhibitors, but there is a problem with these inhibitors in that they degrade the membrane.

Although there is a document (Patent Document 5) that discloses the use of a hypobromous acid solution as a temporary reverse osmosis membrane cleaning agent, because the method uses hypobromous acid itself, even temporary use raises the possibility of membrane degradation. Further, this cleaning application is limited to temporary use, and is fundamentally different from a permanent slime-inhibiting treatment that is continuously kept in contact with the reverse osmosis membrane.

One document (Patent Document 6) also describes the injection of hypobromous acid at a stage prior to a reverse osmosis membrane, but this method also simply uses hypobromous acid itself. Further, the method of Patent Document 6 relates to a method for "pretreatment" of the water flowing into the reverse osmosis membrane, and the hypobromous acid within the water is subjected to a reductive decomposition treatment immediately prior to flowing into the reverse osmosis membrane, meaning the treatment is fundamentally different from a slime inhibition treatment that is continuously kept in contact with the reverse osmosis membrane.

On the other hand, a slime inhibition treatment using a combined chlorine-based oxidizing agent such as chlorosulfamic acid or the like prepared by stabilizing hypochlorous acid with sulfamic acid has also been proposed (Patent Document 7). These combined chlorine-based oxidizing agents have minimal degradation effect on the membrane, but the slime inhibitory effect is unsatisfactory.

Further, in RO devices, in order to inhibit scale, the devices are typically operated with the pH adjusted toward the acidic side (for example, a pH of about 4.0) (for example, see Patent Document 8).

PRIOR ART DOCUMENTS

Patent Documents

Patent Document 1: JP H11-501974 A
Patent Document 2: JP H11-511779 A

Patent Document 3: JP 2002-543048 A
Patent Document 4: JP 2002-516827 A
Patent Document 5: WO 2009/128328 A1
Patent Document 6: JP 2011-050843 A
Patent Document 7: JP 2006-263510 A
Patent Document 8: JP H07-163979 A

SUMMARY OF THE INVENTION

Problems to be Solved by the Invention

An object of the present invention is to provide a method for producing a one-liquid stabilized hypobromous acid composition which contains substantially no bromate ions, has excellent sterilization performance, exhibits almost no corrosiveness relative to metals, and displays excellent storage stability, and also provide a stabilized hypobromous acid composition.

Further, another object of the present invention is to provide a slime inhibition method for a separation membrane, which suppresses degradation of the separation membrane, suppresses any deterioration in the water quality of the treated water (permeate) and the concentrate and the like, and has a satisfactory slime inhibitory effect.

Means for Solving the Problems

The present invention provides a method for producing a stabilized hypobromous acid composition including a step of inducing a reaction by adding bromine, under an inert gas atmosphere, to a mixed solution comprising water, an alkali hydroxide and sulfamic acid, wherein the proportion of bromine added is not more than 25 wt % relative to the total weight of the composition.

Further, in the above method for producing a stabilized hypobromous acid composition, the bromine is preferably reacted under conditions in which the oxygen concentration inside the reaction vessel is controlled to not more than 6%.

Further, in the above method for producing a stabilized hypobromous acid composition, the reaction temperature during addition of the bromine is preferably controlled within a range from at least 0° C. to not more than 25° C.

Furthermore, in the above method for producing a stabilized hypobromous acid composition, the ratio of the equivalent weight of the sulfamic acid relative to the equivalent weight of the bromine is within a range from 1.01 to 1.1.

Further, in the above method for producing a stabilized hypobromous acid composition, the equivalent weight ratio of the sulfamic acid relative to the alkali hydroxide prior to the addition of the bromine is preferably within a range from 0.28 to 0.35.

Further, in the above method for producing a stabilized hypobromous acid composition, the pH of the composition is preferably higher than 13.5.

Further, in the above method for producing a stabilized hypobromous acid composition, an alkali hydroxide is preferably added to the composition to adjust the pH to a value higher than 13.5.

Furthermore, in the above method for producing a stabilized hypobromous acid composition, the inert gas is preferably at least one of nitrogen and argon.

Further, in the above method for producing a stabilized hypobromous acid composition, the alkali hydroxide is preferably at least one of sodium hydroxide and potassium hydroxide.

Further, in the above method for producing a stabilized hypobromous acid composition, the alkali hydroxide is preferably a combination of sodium hydroxide and potassium hydroxide.

Furthermore, the present invention also provides a stabilized hypobromous acid composition produced by a method including a step of inducing a reaction by adding bromine, under an inert gas atmosphere, to a mixed solution comprising water, an alkali hydroxide and sulfamic acid, wherein the proportion of bromine added is not more than 25 wt % relative to the total weight of the composition.

Further, in the above stabilized hypobromous acid composition, the bromate ion content is preferably less than 5 mg/kg.

Moreover, the present invention also provides a slime inhibition method for a separation membrane which includes incorporating a stabilized hypobromous acid composition obtained from the above method for producing a stabilized hypobromous acid composition, or the above stabilized hypobromous acid composition, in a feed water or a wash water supplied to a membrane separation device containing the separation membrane.

Further, in the above slime inhibition method for a separation membrane, the separation membrane is preferably a polyamide-based polymer membrane.

Further, in the above slime inhibition method for a separation membrane, the membrane separation device preferably includes an RO membrane as the separation membrane, and the pH of the feed water supplied to the membrane separation device is preferably 5.5 or higher.

Furthermore, in the above slime inhibition method for a separation membrane, the bromate concentration in the stabilized hypobromous acid composition is preferably less than 5 mg/kg.

Advantages of the Invention

In the present invention, by inducing a reaction by adding bromine, under an inert gas atmosphere, to a mixed solution comprising water, an alkali hydroxide and sulfamic acid, with the proportion of bromine added restricted to not more than 25 wt % relative to the total weight of the composition, a method for producing a one-liquid stabilized hypobromous acid composition which contains substantially no bromate ions, has excellent sterilization performance, exhibits almost no corrosiveness relative to metals, and displays excellent storage stability, and a stabilized hypobromous acid composition, can be provided.

Furthermore, in the present invention, by incorporating a stabilized hypobromous acid composition obtained from the above method for producing a stabilized hypobromous acid composition, or the above stabilized hypobromous acid composition, in a feed water or a wash water supplied to a membrane separation device containing a separation membrane, degradation of the separation membrane, and deterioration in the water quality of the treated water (permeate) and the concentrate and the like can be suppressed, and a satisfactory slime inhibitory effect can be achieved.

BEST MODE FOR CARRYING OUT THE INVENTION

Embodiments of the present invention are described below, but these embodiments are merely examples of implementing the present invention, and the present invention is in no way limited by these embodiments.

As a result of intensive investigation, the inventors of the present invention discovered that by inducing a reaction by adding bromine, under an inert gas atmosphere, to a mixed solution comprising water, an alkali hydroxide and sulfamic acid, preferably under conditions in which the oxygen concentration inside the reaction vessel is controlled to not more than 6%, and restricting the proportion of bromine added to not more than 25 wt % relative to the total weight of the composition, a one-liquid stabilized hypobromous acid composition could be obtained which contains substantially no bromate ions, has excellent sterilization performance, exhibits almost no corrosiveness relative to metals, and displays excellent storage stability. By reacting the bromine under an inert gas atmosphere, and ensuring that the proportion of bromine added is not more than 25 wt % relative to the total weight of the composition, production of bromic acid within the reaction system can be reduced, and the corrosiveness can decrease. The inventors also discovered that the amount of bromic acid produced and the corrosiveness tended to be dependent on the ratio between the equivalent weight of sulfamic acid and the equivalent weight of bromine, the equivalent weight ratio of the sulfamic acid relative to the alkali hydroxide prior to the addition of the bromine, the composition pH, and the reaction temperature and the like, and they finally succeeded in developing a one-liquid stabilized hypobromous acid composition for controlling biofouling in aqueous systems which contains substantially no bromate ions, has excellent sterilization performance, exhibits almost no corrosiveness relative to metals, and displays excellent storage stability, as well as a method for producing this composition.

The stabilized hypobromous acid composition according to an embodiment of the present invention comprises mainly sulfamic acid-sodium hypobromite salts ($^-O-SO_2-NH-Br$, $^-O-SO_2-NBr_2$ and other stabilized hypobromite salts). The stabilized hypobromous acid composition according to this embodiment can be obtained by inducing a reaction by adding bromine, under an inert gas atmosphere, to a mixed solution comprising water, an alkali hydroxide and sulfamic acid.

One essential factor in the method for producing a stabilized hypobromous acid composition according to the present embodiment is the conducting of the reaction of the bromine with the mixed solution comprising water, an alkali hydroxide and sulfamic acid under an inert gas atmosphere. Although Patent Document 3 discloses that "the step of adding bromine or bromine chloride is performed without exposing the bromine to air", no mention is made of the method used for removing the oxygen inside the reaction vessel. Similarly, Patent Document 3 discloses that "bromine is preferably added directly into the stabilized solution through a Teflon (a registered trademark) tube to prevent elemental bromine exposure to air", but no mention is made of the method used for removing the oxygen inside the reaction vessel, and this disclosure does not represent means for removing oxygen from inside the reaction vessel. In contrast, if the reaction is performed with the air inside the reaction vessel replaced with an inert gas, then the effect of partial pressure forces oxygen out of the solution, meaning the bromic acid production reaction represented by the formula shown below hardly proceeds at all.

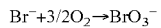

$Br^- + 3/2 O_2 \rightarrow BrO_3^-$

The oxygen concentration inside the reaction vessel during the bromine reaction is preferably not more than 6%, more preferably not more than 4%, still more preferably not more than 2%, and most preferably 1% or less. If the oxygen concentration inside the reaction vessel during the bromine reaction exceeds 6%, then the amount of bromic acid produced in the reaction system may increase.

Although there are no particular limitations on the inert gas used during the reaction, at least one of nitrogen and argon is preferred from a production perspective and the like, and nitrogen is particularly preferred in terms of production costs and the like.

Bubbling the inert gas through the solution or reducing the pressure inside the reaction vessel are effective in removing oxygen from inside the reaction vessel.

The proportion of bromine added is not more than 25 wt % relative to the total weight of the composition, and is more preferably at least 1 wt % but not more than 20 wt %. If the proportion of bromine added exceeds 25 wt % relative to the total weight of the composition, then the control of biofouling may deteriorate. If the proportion is less than 1%, then the control of biofouling may deteriorate.

The ratio of the equivalent weight of sulfamic acid relative to the equivalent weight of bromine is preferably within a range from 1.01 to 1.1, and is more preferably within a range from 1.02 to 1.05. If the ratio of the equivalent weight of sulfamic acid relative to the equivalent weight of bromine is less than 1.01, then the amount of bromic acid produced in the reaction system may sometimes increase, whereas if the ratio exceeds 1.1, then the corrosiveness may increase.

The pH of the composition is preferably higher than 13.5, and more preferably higher than 13.7. If the pH of the composition is 13.5 or lower, then the corrosiveness may sometimes increase.

The total amount of the alkali hydroxide may be added prior to the addition of bromine, or alternatively, in order to improve the precision of the final pH, a portion of the alkali hydroxide may be added to the composition after the addition of bromine to adjust the pH of the composition to a value higher than 13.5. However, the mixed solution comprising water, the alkali hydroxide and sulfamic acid preferably has a pH of 7 or higher.

For the alkali hydroxide, other alkali hydroxides such as potassium hydroxide may also be used, either instead of, or in combination with, sodium hydroxide. In terms of achieving good product stability and the like at low temperatures, the use of a combination of sodium hydroxide and potassium hydroxide is particularly preferred. The alkali hydroxide may be used in solid form, or may be used in the form of an aqueous solution.

For reasons including controlling heat generation, it is possible to add the alkali hydroxide in portions, before and after the addition of bromine, but in such cases, the sodium sulfamate solution preferably has a pH of 7 or higher prior to the addition of bromine.

Further, if the solution is highly alkaline prior to the addition of bromine, then there is a possibility that bromate ions may be produced, and therefore the equivalent weight ratio of sulfamic acid relative to the alkali hydroxide prior to the addition of bromine is preferably within a range from 0.28 to 0.35. If the equivalent weight ratio of sulfamic acid relative to the alkali hydroxide prior to the addition of bromine is less than 0.28, then bromate ions may sometimes be produced, whereas if the ratio exceeds 0.35, then the corrosiveness may increase.

The reaction temperature during the bromine addition is preferably controlled within a range from at least 0° C. to not more than 25° C., and in terms of production costs and the like, is more preferably controlled within a range from at least 0° C. to not more than 15° C. If the reaction temperature during the bromine addition exceeds 25° C., then the amount of bromic acid produced in the reaction system may sometimes increase, whereas if the temperature is less than 0° C., then the reaction system may freeze.

By using the method for producing a stabilized hypobromous acid composition according to the present embodiment, the composition of mainly sulfamic acid-sodium hypobromite salts contains substantially no bromate ions, and moreover, even if the composition is brought into contact with metal materials, then almost no corrosion occurs, meaning the composition can be handled safely.

The stabilized hypobromous acid composition obtained from the method for producing a stabilized hypobromous acid composition according to the present embodiment contains substantially no bromate ions, and the bromate ion content is, for example, less than 5 mg/kg. In this description, the expression "contains substantially no bromate ions" means that the bromate ion content is less than the detection limit when analyzed using an analysis technique that represents the best available technology (BAT). In Patent Document 3, an ion chromatography method is used as the method for analyzing bromate ions, and the lower detection limit for this method is disclosed as being less than 50 mg/L, but if the post-column ion chromatography method used by the inventors of the present invention is used, then a lower detection limit of 5 mg/kg can be achieved, meaning bromate ion concentrations of 5 to 50 mg/kg can be detected. Further, in the actual Examples described below, bromate ions were detected at concentrations of 5 to 50 mg/kg in some stabilized hypobromous acid compositions. In the "Guidelines for Test Methods for Evaluating Chemicals in Water" compiled under the supervision of the Ministry of Health, Labor and Welfare based on the Water Supply Act, the evaluation standard for bromic acid is prescribed as 0.005 mg/L, and if it is considered that the stabilized hypobromous acid composition according to the present embodiment may be used, for example, at a dilution of 10,000 to 100,000-fold, then the ability to detect bromate ions of 5 to 50 mg/kg in the composition, and the ability to achieve a bromate ion content within the composition of less than 5 mg/kg are extremely significant.

The effective bromine concentration contained in the composition is preferably within a range from 1 wt % to 25 wt %, and more preferably within a range from 1 wt % to 20 wt %, relative to the total weight of the composition. If the effective bromine concentration is less than 1 wt % relative to the total weight of the composition, then the composition may exhibit inferior control of biofouling, whereas if the concentration exceeds 25 wt %, then the amount of bromic acid produced in the reaction system may sometimes increase.

It is desirable that almost no corrosion occurs when a composition for controlling biofouling in an aqueous system is brought into contact with a metal material. The composition for controlling biofouling in the aqueous system is often injected into the system using a chemical injection device, and because the composition is used as a neat liquid without dilution, it is desirable to avoid troubles such as corrosion of the injection line, and corrosion of the connection line between the chemical feed line and the water treatment system that represents the target. Actual corrosion troubles caused by sodium hypochlorite solutions or the like have yet to be fundamentally resolved, but for example even Patent Document 3 discloses that stable oxidizing bromine formulations are "corrosive solutions" and actual results confirming high metal corrosiveness have been obtained.

The standard for ascertaining that almost no corrosion occurs when the stabilized hypobromous acid composition is brought into contact with a metal material is preferably a value of less than 1 for the corrosion rate (mdd) described below.

In this manner, the method for producing a stabilized hypobromous acid composition according to the present embodiment yields a one-liquid stabilized hypobromous acid composition which contains substantially no bromate ions, has excellent sterilization performance, exhibits almost no corrosiveness relative to metals, and displays excellent storage stability.

The stabilized hypobromous acid composition according to the present embodiment can be used, for example, as a fungicide for controlling biofouling in aqueous systems including industrial water systems such as water-cooling systems and papermaking processes.

<Slime Inhibition Method for Separation Membrane>

The slime inhibition method for a separation membrane according to one embodiment of the present invention is a method of incorporating a stabilized hypobromous acid composition obtained from the above method for producing a stabilized hypobromous acid composition in a feed water or a wash water supplied to a membrane separation device containing the separation membrane.

Further, the slime inhibition method for a separation membrane according to an embodiment of the present invention is a method of incorporating a "bromine-based oxidizing agent", or a "reaction product of a bromine compound and a chlorine-based oxidizing agent", and a "sulfamic acid compound", in a feed water or a wash water supplied to a membrane separation device containing the separation membrane. It is thought that, as a result, a stabilized hypobromous acid composition is formed within the feed water or wash water.

Furthermore, the slime inhibition method for a separation membrane according to an embodiment of the present invention is a method of incorporating a stabilized hypobromous acid composition comprising a "reaction product of a bromine-based oxidizing agent and a sulfamic acid compound", or a "reaction product of a sulfamic acid compound with a reaction product of a bromine compound and a chlorine-based oxidizing agent", in a feed water or a wash water supplied to a membrane separation device containing the separation membrane.

Specifically, the slime inhibition method for a separation membrane according to an embodiment of the present invention is a method of incorporating, for example, "bromine", "bromine chloride" or a "reaction product of sodium bromide and hypochlorous acid", and a "sulfamic acid compound" in a feed water or a wash water supplied to a membrane separation device containing the separation membrane.

Further, the slime inhibition method for a separation membrane according to an embodiment of the present invention is a method of incorporating, for example, a "reaction product of bromine and a sulfamic acid compound", a "reaction product of bromine chloride and a sulfamic acid compound" or a "reaction product of a sulfamic acid compound with a reaction product of sodium bromide and hypochlorous acid" in a feed water or a wash water supplied to a membrane separation device containing the separation membrane.

By incorporating a stabilized hypobromous acid composition obtained from the above method for producing a stabilized hypobromous acid composition, by incorporating a "bromine-based oxidizing agent", or a "reaction product of a bromine compound and a chlorine-based oxidizing agent", and a "sulfamic acid compound", or by incorporating a reaction product of these components, slime on the separation membrane can be inhibited. Further, membrane contamination by microbes can be reliably inhibited, with almost no deterioration in the performance of the separation membrane. By using the slime inhibition method for a separation membrane according to the present embodiment, a slime inhibition treatment having a superior slime inhibitory effect can be achieved while suppressing any effects on the membrane performance and the water quality in subsequent stages to a minimum.

For example, the stabilized hypobromous acid composition obtained from the above method for producing a stabilized hypobromous acid composition may be injected into the feed water or a wash water supplied to the membrane separation device using a chemical feed pump or the like.

In another example, a "bromine-based oxidizing agent", or a "reaction product of a bromine compound and a chlorine-based oxidizing agent", and a "sulfamic acid compound" may be injected into the feed water or a wash water supplied to the membrane separation device using a chemical feed pump or the like. The "bromine-based oxidizing agent", or "reaction product of a bromine compound and a chlorine-based oxidizing agent", and the "sulfamic acid compound" may be added to the aqueous system separately, or the neat liquids may be mixed together and then added to the aqueous system.

In yet another example, a "reaction product of a bromine-based oxidizing agent and a sulfamic acid compound" or a "reaction product of a sulfamic acid compound with a reaction product of a bromine compound and a chlorine-based oxidizing agent" may be injected into the feed water or a wash water supplied to the membrane separation device using a chemical feed pump or the like.

The ratio of the equivalent weight of the "sulfamic acid compound" relative to the equivalent weight of the "bromine-based oxidizing agent" or the "reaction product of a bromine compound and a chlorine-based oxidizing agent" is preferably 1 or greater, and is more preferably within a range from at least 1 to not more than 2. If the ratio of the equivalent weight of the "sulfamic acid compound" relative to the equivalent weight of the "bromine-based oxidizing agent" or the "reaction product of a bromine compound and a chlorine-based oxidizing agent" is less than 1, then there is a possibility that degradation of the membrane may occur, whereas if the ratio exceeds 2, then the production costs may sometimes increase.

The effective halogen concentration contacting the separation membrane, calculated as an effective equivalent chlorine concentration, is preferably from 0.01 to 100 mg/L. If this concentration is less than 0.01 mg/L, then a satisfactory slime inhibitory effect may not be obtainable, whereas if the concentration is greater than 100 mg/L, then there is a possibility that degradation of the separation membrane or corrosion of the piping or the like may occur.

Examples of the bromine-based oxidizing agent include bromine (liquid bromine), bromine chloride, bromic acid, and bromate salts and the like.

Among these, compared with the formulation of "hypochlorous acid, a bromine compound and sulfamic acid" and the formulation of "bromine chloride and sulfamic acid" and the like, formulations that use bromine such as "bromine and a sulfamic acid compound" or a "reaction product of bromine and a sulfamic acid compound" can exhibit less degradation of RO membranes and the like, and suffer from less leakage of effective halogen into the membrane permeate such as the RO permeate, and are consequently preferred as slime inhibitors for separation membranes such as RO membranes.

In other words, the slime inhibition method for a separation membrane according to one embodiment of the present invention is preferably a method of incorporating bromine and a sulfamic acid compound in the feed water or a wash water supplied to a membrane separation device containing the separation membrane. Further, incorporating a reaction product of bromine and a sulfamic acid compound in the feed water or a wash water supplied to a membrane separation device containing the separation membrane is also preferred.

Examples of the bromine compound include sodium bromide, potassium bromide, lithium bromide and hydrobromic acid. Among these, in terms of production costs and the like, sodium bromide is preferred.

Examples of the chlorine-based oxidizing agent include chlorine gas, chlorine dioxide, hypochlorous acid or salts thereof, chlorous acid or salts thereof, chloric acid or salts thereof, perchloric acid or salts thereof, and chlorinated isocyanuric acid or salts thereof. Among these, examples of the salts include alkali metal salts of hypochlorous acid such as sodium hypochlorite and potassium hypochlorite, alkaline earth metal salts of hypochlorous acid such as calcium hypochlorite and barium hypochlorite, alkali metal salts of chlorous acid such as sodium chlorite and potassium chlorite, alkaline earth metal salts of chlorous acid such as barium chlorite, other metal salts of chlorous acid such as nickel chlorite, alkali metal salts of chloric acid such as ammonium chlorate, sodium chlorate and potassium chlorate, and alkaline earth metal salts of chloric acid such as calcium chlorate and barium chlorate. Any one of these chlorine-based oxidizing agents may be used alone, or a combination of two or more oxidizing agents may be used. In terms of ease of handling and the like, the use of sodium hypochlorite as the chlorine-based oxidizing agent is preferred.

The sulfamic acid compound is a compound represented by general formula (1) shown below.

$$R_2NSO_3H \quad (1)$$

(In the formula, each R independently represents a hydrogen atom or an alkyl group having a carbon number of 1 to 8.)

Examples of the sulfamic acid compound, in addition to sulfamic acid (amidosulfuric acid) in which the two R groups are both hydrogen atoms, include sulfamic acid compounds in which one of the two R groups is a hydrogen atom and the other is an alkyl group having a carbon number of 1 to 8, such as N-methylsulfamic acid, N-ethylsulfamic acid, N-propylsulfamic acid, N-isopropylsulfamic acid and N-butylsulfamic acid, sulfamic acid compounds in which the two R groups are both alkyl groups having a carbon number of 1 to 8, such as N,N-dimethylsulfamic acid, N,N-diethylsulfamic acid, N,N-dipropylsulfamic acid, N,N-dibutylsulfamic acid, N-methyl-N-ethylsulfamic acid and N-methyl-N-propylsulfamic acid, and sulfamic acid compounds in which one of the two R groups is a hydrogen atom and the other is an aryl group having a carbon number of 6 to 10, such as N-phenylsulfamic acid, as well as salts of the above acids. Examples of the sulfamic acid salts include alkali metal salts such as sodium salts and potassium salts, alkaline earth metal salts such as calcium salts, strontium salts and barium salts, other metal salts such as manganese salts, copper salts, zinc salts, iron salts, cobalt salts and nickel salts, as well as ammonium salts and guanidine salts.

One of these sulfamic acid compounds or salts may be used alone, or a combination of two or more compounds or salts may be used. In terms of the environmental burden and the like, the use of sulfamic acid (amidosulfuric acid) as the sulfamic acid compound is preferred.

In the slime inhibition method for a separation membrane according to the present embodiment, an alkali is preferably also included. Examples of the alkali include alkali hydroxides such as sodium hydroxide and potassium hydroxide. In terms of achieving good product stability and the like at low temperatures, a combination of sodium hydroxide and potassium hydroxide may also be used. The alkali is typically used not as a solid, but in the form of an aqueous solution.

Examples of the separation membrane include a reverse osmosis membrane (RO membrane), nanofiltration membrane (NF membrane), microfiltration membrane (MF membrane), and ultrafiltration membrane (UF membrane). Among these, the slime inhibition method for a separation membrane according to an embodiment of the present invention can be applied particularly favorably to reverse osmosis membranes (RO membranes). Further, the slime inhibition method for a separation membrane according to an embodiment of the present invention can be used favorably with polyamide-based polymer membranes, which are currently the most widely used reverse osmosis membranes. Polyamide-based polymer membranes have comparatively low resistance to oxidizing agents, and if free chlorine or the like is kept in continuous contact with a polyamide-based polymer membrane, then a marked deterioration may occur in the performance of the membrane. However, in the slime inhibition method for a separation membrane according to the present embodiment, this type of marked deterioration in the membrane performance is almost non-existent, even for polyamide polymer membranes.

In the slime inhibition method for a separation membrane according to the present embodiment, in the case where the membrane separation device is an RO device having an RO membrane as the separation membrane, the pH of the feed water supplied to the RO device is preferably 5.5 or higher, more preferably 6.0 or higher, and still more preferably 6.5 or higher. If the pH of the feed water supplied to the RO device is less than 5.5, then the volume of permeate may sometimes decrease. Further, there are no particular limitations on the upper limit for the pH of the feed water supplied to the RO device, provided that the pH is no higher than the typical upper limit pH for RO devices (for example, pH 10), but if scale deposition of hard components such as calcium is also considered, then operating the RO device at a pH of, for example, 9.0 or lower is preferred. When the slime inhibition method for a separation membrane according to the present embodiment is used, by operating the RO device with the pH of the feed water supplied to the device set to 5.5 or higher, degradation of the RO membrane and deterioration in the quality of the treated water (permeate) can be suppressed, a satisfactory slime inhibitory effect can be achieved, and a satisfactory permeate volume can also be ensured.

In those cases where scale develops in the RO device when the pH of the feed water supplied to the RO device is 5.5 or higher, a dispersant may be used in combination with the stabilized hypobromous acid composition for the purpose of scale inhibition. Examples of the dispersant include polyacrylic acid, polymaleic acid and phosphonic acid. The amount of the dispersant added to the feed water, for example in terms of the concentration within the RO concentrate, is typically within a range from 0.1 to 1,000 mg/L.

Further, one method for inhibiting the occurrence of scale without using a dispersant involves adjusting the operating conditions for the RO device such as the recovery rate so that the silica concentration in the RO concentrate is no higher than the degree of solubility, and the Langelier index, which is an indicator for calcium scale, is not more than 0.

Examples of applications for RO devices include seawater desalination and wastewater recovery.

<Slime-Inhibiting Composition for Separation Membrane>

A slime-inhibiting composition for a separation membrane according to this embodiment is a composition comprising the stabilized hypobromous acid composition obtained from the above method for producing a stabilized hypobromous acid composition, and may also include an alkali.

Further, the slime-inhibiting composition for a separation membrane according to this embodiment may also be a composition comprising a "bromine-based oxidizing agent", or a "reaction product of a bromine compound and a chlorine-based oxidizing agent", and a "sulfamic acid compound", and may also include an alkali.

Furthermore, the slime-inhibiting composition for a separation membrane according to this embodiment may also be a composition comprising a "reaction product of a bromine-based oxidizing agent and a sulfamic acid compound" or a "reaction product of a sulfamic acid compound with a reaction product of a bromine compound and a chlorine-based oxidizing agent", and may also include an alkali.

The bromine-based oxidizing agent, the bromine compound, the chlorine-based oxidizing agent, and the sulfamic acid compound are as described above.

The slime-inhibiting composition for a separation membrane according to the present embodiment is preferably a composition comprising bromine and a sulfamic acid compound, or a composition comprising a reaction product of bromine and a sulfamic acid compound, as such compositions can exhibit less degradation of RO membranes and the like, and suffer from less leakage of effective halogen into the membrane permeate such as the RO permeate.

Compared with combined chlorine-based slime inhibitors such as chlorosulfamic acid, the slime-inhibiting composition for a separation membrane according to the present embodiment can have higher oxidizing power, and markedly higher slime inhibition and slime-detaching power, and yet cause almost none of the marked membrane degradation observed for other compositions of similar oxidizing power such as hypochlorous acid and hypobromous acid. At typical usage concentrations, the effects on membrane degradation can be substantially ignored. As a result, the composition is ideal as a slime inhibitor for separation membranes such as RO membranes.

Unlike hypochlorous acid, the slime-inhibiting composition for a separation membrane according to the present embodiment can undergo almost no permeation through the RO membrane, and therefore have almost no effect on the treated water quality. Further, because the concentration can be measured on site in a similar manner to hypochlorous acid or the like, more accurate concentration control is possible.

The pH of the composition is, for example, higher than 13.0, and is preferably higher than 13.2. If the pH of the composition is 13.0 or lower, then the effective halogen in the composition may sometimes become unstable.

The bromate concentration in the slime-inhibiting composition for a separation membrane is preferably less than 5 mg/kg. If the bromate concentration in the slime-inhibiting composition for a separation membrane is 5 mg/kg or greater, then the concentration of bromate ions in the permeate may increase.

<Method for Producing Slime-Inhibiting Composition for Separation Membrane>

The slime-inhibiting composition for a separation membrane according to an embodiment of the present invention is obtained by mixing a bromine-based oxidizing agent and a sulfamic acid compound, or by mixing a reaction product of a bromine compound and a chlorine-based oxidizing agent, and a sulfamic acid compound. An alkali may also be mixed into the composition.

The method for producing a slime-inhibiting composition for a separation membrane that comprises bromine and a sulfamic acid compound, or a slime-inhibiting composition for a separation membrane that comprises a reaction product of bromine and a sulfamic acid compound preferably includes a step of adding bromine, under an inert gas atmosphere, to a mixed solution comprising water, an alkali and a sulfamic acid compound. By performing the addition and inducing the reaction under an inert gas atmosphere, the concentration of bromate ions in the composition can be reduced, and the bromate ion concentration in the permeate such as the RO permeate can be also reduced.

Although there are no particular limitations on the inert gas used, at least one of nitrogen and argon is preferred from a production perspective and the like, and nitrogen is particularly preferred in terms of production costs and the like.

The oxygen concentration inside the reaction vessel during the bromine addition is preferably not more than 6%, more preferably not more than 4%, still more preferably not more than 2%, and most preferably 1% or less. If the oxygen concentration inside the reaction vessel during the bromine reaction exceeds 6%, then the amount of bromic acid produced in the reaction system may sometimes increase.

The proportion of bromine added is preferably not more than 25 wt % relative to the total weight of the composition, and is more preferably at least 1 wt % but not more than 20 wt %. If the proportion of bromine added exceeds 25 wt % relative to the total weight of the composition, then the amount of bromic acid produced in the reaction system may sometimes increase. If the proportion is less than 1 wt %, then the sterilizing power may be poor.

The reaction temperature during the bromine addition is preferably controlled within a range from at least 0° C. to not more than 25° C., and in terms of production costs and the like, is more preferably controlled within a range from at least 0° C. to not more than 15° C. If the reaction temperature during the bromine addition exceeds 25° C., then the amount of bromic acid produced in the reaction system may sometimes increase, whereas if the temperature is less than 0° C., then the reaction system may freeze.

EXAMPLES

The present invention is described below in further detail using a series of Examples and Comparative Examples, but the present invention is in no way limited by these examples.

Example 1

A 2 liter four-necked flask into which nitrogen gas was injected continuously at a flow rate controlled by a mass flow controller so that the oxygen concentration inside the reaction vessel was maintained at 1% was charged with 1,453 g of water and 361 g of sodium hydroxide, and following mixing, 300 g of sulfamic acid was added and mixed, and with the flask then cooled to maintain the temperature of the reaction solution at 0 to 15° C., 456 g of liquid bromine was added, and 230 g of a 48% solution of potassium hydroxide was then added, thus obtaining the target stabilized hypobromous acid composition containing 10.7 wt % of sulfamic acid and 16.3 wt % of bromine relative to the total weight of the composition, and having a ratio for the equivalent weight of sulfamic acid relative to the equivalent weight of bromine of 1.08. Measurement of the pH of the prepared solution using the glass electrode method yielded a value of 14.0. Measurement of the bromine content of the prepared solution using a method in which the bromine was substituted with iodine using potassium iodide, and a redox titration was then performed using sodium thiosulfate revealed a value of 16.3%, which was 100.0% of the theoretical content (16.3%). Further, the oxygen concentration inside the reaction vessel during the bromine reaction was measured using an "Oxygen Monitor JKO-02 LJDII" manufactured by Jikco Ltd.

The result of measuring the bromate ion concentration in the undiluted solution produced in Example 1 using a post-column ion chromatography method in accordance with the analysis method prescribed in "JWWA K 120 (2008) Sodium hypochlorite for water supply, 5.4.5 Bromic acid" yielded a bromate ion concentration less than the lower detection limit of 5 mg/kg.

A corrosion test was performed by immersing a metal test piece in the undiluted solution produced in Example 1. This corrosion test was performed in accordance with "JIS K 0100 Testing method for corrosivity of industrial water".

[Test Conditions]

Test piece: SS-400 (#400)
Test piece surface area: 0.01 dm$^2$ (1 mm×10 mm×10 mm)
Test temperature: 25° C.
Test period: 3 days
Evaluation item: corrosion rate (mdd)

In relation to the corrosion rate, following completion of the test, the test piece (SS-400) was washed with 15% hydrochloric acid to which an acid wash corrosion inhibitor ("Ibit" manufactured by Asahi Chemical Co., Ltd.) had been added, the reduction in mass of the test piece was determined, and when the number of mg of mass reduction due to corrosion per 1 dm$^2$ of surface area of the test piece per day, namely mdd (mg/dm$^2$·day) was calculated using the formula shown below, the result was 0.4.

$$W=(M1-M2)/(S\times T)$$

In this formula, W represents the corrosion rate (mdd), M1 represents the mass (mg) of the test piece prior to the test, M2 represents the mass (mg) of the test piece following the test, S represents the surface area (dm$^2$) of the test piece, and T represents the number of days of the test.

Example 2

When synthesis was performed under the same conditions as Example 1, but with the flow rate of the nitrogen gas controlled by the mass flow controller so that the oxygen concentration inside the reaction vessel was maintained at 4%, the bromate ion concentration in the undiluted solution was less than the lower detection limit of 5 mg/kg. Further, the corrosion rate (mdd) measured by the corrosion test was 0.6.

Examples 3 to 35, Comparative Examples 1 to 7

Using the conditions shown in Table 1, samples were synthesized in the same manner as Example 1, and the bromate ion concentration and the corrosiveness (corrosion rate) were evaluated. The oxygen concentration when inert gas substitution was not performed was not measured, but is assumed to be about 21%, namely the oxygen concentration in the atmosphere. The results are shown in Tables 1 and 2.

TABLE 1

| | Composition formulation | | | | | | | Reaction conditions | |
|---|---|---|---|---|---|---|---|---|---|
| | Pure water wt % | Sodium hydroxide wt % | 48% potassium hydroxide wt % | Sulfamic acid wt % | Bromine wt % | Sodium hydroxide wt % | 48% potassium hydroxide wt % | Equivalent weight ratio of sulfamic acid relative to alkali hydroxide prior to bromine addition | Equivalent weight ratio [sulfamic acid]/[bromine] |
| Example 1 | 51.9 | 12.9 | | 10.7 | 16.3 | | 8.2 | 0.34 | 1.08 |
| Example 2 | 51.9 | 12.9 | | 10.7 | 16.3 | | 8.2 | 0.34 | 1.08 |
| Example 3 | 51.9 | 12.9 | | 10.7 | 16.3 | | 8.2 | 0.34 | 1.08 |
| Example 4 | 51.6 | 12.9 | | 10.7 | 16.6 | | 8.2 | 0.34 | 1.06 |
| Example 5 | 51.6 | 12.9 | | 10.7 | 16.6 | | 8.2 | 0.34 | 1.06 |
| Example 6 | 51.6 | 12.9 | | 10.7 | 16.6 | | 8.2 | 0.34 | 1.06 |
| Example 7 | 51.3 | 12.9 | | 10.7 | 16.9 | | 8.2 | 0.34 | 1.04 |
| Example 8 | 51.3 | 12.9 | | 10.7 | 16.9 | | 8.2 | 0.34 | 1.04 |
| Example 9 | 51.3 | 12.9 | | 10.7 | 16.9 | | 8.2 | 0.34 | 1.04 |
| Example 10 | 54.9 | 17.5 | | 10.7 | 16.9 | | | 0.25 | 1.04 |
| Example 11 | 49.8 | 11.5 | | 10.7 | 16.9 | | 11.1 | 0.38 | 1.04 |
| Comparative Example 1 | 51.9 | 12.9 | | 10.7 | 16.3 | | 8.2 | 0.34 | 1.08 |
| Comparative Example 2 | 51.6 | 12.9 | | 10.7 | 16.6 | | 8.2 | 0.34 | 1.06 |
| Comparative Example 3 | 51.3 | 12.9 | | 10.7 | 16.9 | | 8.2 | 0.34 | 1.04 |
| Comparative Example 4 | 64.98 | 8.95 | | 9.87 | 16.20 | | | 0.45 | 1.00 |
| Comparative Example 5 | 58.33 | 8.95 | | 9.87 | 16.20 | 6.65 | | 0.45 | 1.00 |
| Comparative Example 6 | 52.83 | 8.95 | | 9.87 | 16.20 | 12.15 | | 0.45 | 1.00 |
| Example 12 | 51.3 | 12.9 | | 10.7 | 16.9 | | 8.2 | 0.34 | 1.04 |
| Example 13 | 51.3 | 12.9 | | 10.7 | 16.9 | | 8.2 | 0.34 | 1.04 |
| Example 14 | 51.3 | 12.9 | | 10.7 | 16.9 | | 8.2 | 0.34 | 1.04 |
| Example 15 | 25.9 | | 38.3 | 10.7 | 16.9 | | 8.2 | 0.34 | 1.04 |

| | Reaction conditions | | | | Composition | | Evaluation |
|---|---|---|---|---|---|---|---|
| | Reaction solution temperature during bromine dropwise addition ° C. | Nitrogen purge | Argon purge | Oxygen concentration inside reaction vessel | pH | Effective bromine concentration wt % | Bromate ion concentration mg/kg | Immersion corrosion test mdd |
| Example 1 | 0 to 15 | yes | | 1% | 14 | 16.3 | <5 | 0.4 |
| Example 2 | 0 to 15 | yes | | 4% | 14 | 16.3 | <5 | 0.6 |
| Example 3 | 0 to 15 | | yes | 4% | 14 | 16.3 | <5 | 0.8 |
| Example 4 | 0 to 15 | yes | | 1% | 14 | 16.6 | <5 | 0.6 |
| Example 5 | 0 to 15 | yes | | 4% | 14 | 16.6 | <5 | 0.6 |
| Example 6 | 0 to 15 | | yes | 4% | 14 | 16.6 | <5 | 0.7 |
| Example 7 | 0 to 15 | yes | | 1% | 14 | 16.9 | <5 | 0.5 |
| Example 8 | 0 to 15 | yes | | 4% | 14 | 16.9 | <5 | 0.7 |
| Example 9 | 0 to 15 | | yes | 4% | 14 | 16.9 | <5 | 0.8 |
| Example 10 | 0 to 15 | yes | | 4% | 14 | 16.8 | 7 | 0.6 |
| Example 11 | 0 to 15 | yes | | 4% | 14 | 16.8 | 8 | 0.8 |
| Comparative Example 1 | 0 to 15 | no | | — | 14 | 16.1 | 56 | 0.4 |
| Comparative Example 2 | 0 to 15 | no | | — | 14 | 16.4 | 60 | 0.9 |
| Comparative Example 3 | 0 to 15 | no | | — | 14 | 16.6 | 63 | 0.8 |
| Comparative Example 4 | 0 to 15 | no | | — | 10.1 | 16.1 | 46 | 3497.6 |
| Comparative Example 5 | 0 to 15 | no | | — | 13.4 | 16.0 | 71 | 32.4 |
| Comparative Example 6 | 0 to 15 | no | | — | 14 | 16.0 | 62 | 12.4 |
| Example 12 | 0 to 15 | yes | | 4% | 14 | 16.9 | <5 | 0.8 |
| Example 13 | 15 to 25 | yes | | 4% | 14 | 16.9 | <5 | 0.9 |
| Example 14 | >25, ≤35 | yes | | 4% | 14 | 16.8 | 48.0 | 12.3 |
| Example 15 | 0 to 15 | yes | | 4% | 14 | 16.9 | <5 | 0.8 |

TABLE 2

| | Composition formulation | | | | | | Reaction conditions | |
|---|---|---|---|---|---|---|---|---|
| | Pure water wt % | Sodium hydroxide wt % | 48% potassium hydroxide wt % | Sulfamic acid wt % | Bromine wt % | Sodium hydroxide wt % | 48% potassium hydroxide wt % | Equivalent weight ratio of sulfamic acid relative to alkali hydroxide prior to bromine addition | Equivalent weight ratio [sulfamic acid]/[bromine] |
| Example 16 | 56.7 | 12.9 | | 10.7 | 16.9 | 2.8 | | 0.34 | 1.04 |
| Example 17 | 32.3 | | 37.3 | 10.7 | 16.9 | 2.8 | | 0.35 | 1.04 |
| Example 18 | 56.7 | 15.7 | | 10.7 | 16.9 | | | 0.28 | 1.04 |
| Example 19 | 25.7 | | 46.7 | 10.7 | 16.9 | | | 0.28 | 1.04 |
| Example 20 | 50.8 | 12.9 | | 10.7 | 17.4 | | 8.2 | 0.34 | 1.01 |
| Example 21 | 51.3 | 12.9 | | 10.7 | 16.9 | | 8.2 | 0.34 | 1.04 |
| Example 22 | 52.2 | 12.9 | | 10.7 | 16.0 | | 8.2 | 0.34 | 1.10 |
| Example 23 | 55.0 | 12.9 | | 10.7 | 17.4 | | 4.0 | 0.34 | 1.01 |
| Example 24 | 55.5 | 12.9 | | 10.7 | 16.9 | | 4.0 | 0.34 | 1.04 |
| Example 25 | 56.4 | 12.9 | | 10.7 | 16.0 | | 4.0 | 0.34 | 1.10 |
| Example 26 | 55.8 | 12.9 | | 10.7 | 17.4 | | 3.2 | 0.34 | 1.01 |
| Example 27 | 56.3 | 12.9 | | 10.7 | 16.9 | | 3.2 | 0.34 | 1.04 |
| Example 28 | 57.2 | 12.9 | | 10.7 | 16.0 | | 3.2 | 0.34 | 1.10 |
| Example 29 | 50.2 | 12.9 | | 10.7 | 18.0 | | 8.2 | 0.34 | 0.98 |
| Example 30 | 52.83 | 8.95 | | 9.87 | 16.20 | | 12.15 | 0.45 | 1.00 |
| Example 31 | 53.1 | 12.9 | | 10.7 | 15.1 | | 8.2 | 0.34 | 1.17 |
| Example 32 | 58.33 | 8.95 | | 9.87 | 16.20 | | 6.65 | 0.45 | 1.00 |
| Example 33 | 56.8 | 12.9 | | 10.7 | 16.9 | | 2.7 | 0.34 | 1.04 |
| Example 34 | 58.6 | 12.9 | | 10.7 | 15.1 | | 2.7 | 0.34 | 1.17 |
| Example 35 | 46.3 | 14.1 | | 14.6 | 20.8 | 4.2 | | 0.43 | 1.16 |
| Comparative Example 7 | 34.9 | 20.8 | | 17.0 | 26.8 | 0.5 | | 0.34 | 1.04 |

| | Reaction conditions | | | | Composition | | Evaluation |
|---|---|---|---|---|---|---|---|
| | Reaction solution temperature during bromine dropwise addition °C. | Nitrogen purge | Argon purge | Oxygen concentration inside reaction vessel | pH | Effective bromine concentration wt % | Bromate ion concentration mg/kg | Immersion corrosion test mdd |
| Example 16 | 0 to 15 | yes | | 4% | 14 | 16.9 | <5 | 0.6 |
| Example 17 | 0 to 15 | yes | | 4% | 14 | 16.9 | <5 | 0.6 |
| Example 18 | 0 to 15 | yes | | 4% | 14 | 16.9 | <5 | 0.6 |
| Example 19 | 0 to 15 | yes | | 4% | 14 | 16.9 | <5 | 0.6 |
| Example 20 | 0 to 15 | yes | | 4% | 14 | 17.4 | <5 | 0.8 |
| Example 21 | 0 to 15 | yes | | 4% | 14 | 16.9 | <5 | 0.8 |
| Example 22 | 0 to 15 | yes | | 4% | 14 | 16.0 | <5 | 0.7 |
| Example 23 | 0 to 15 | yes | | 2% | 13.8 | 17.4 | <5 | 0.7 |
| Example 24 | 0 to 15 | yes | | 4% | 13.8 | 16.9 | <5 | 0.6 |
| Example 25 | 0 to 15 | yes | | 2% | 13.8 | 16.0 | <5 | 0.8 |
| Example 26 | 0 to 15 | yes | | 1% | 13.6 | 17.4 | <5 | 0.6 |
| Example 27 | 0 to 15 | yes | | 2% | 13.6 | 16.9 | <5 | 0.5 |
| Example 28 | 0 to 15 | yes | | 1% | 13.6 | 16.0 | <5 | 0.6 |
| Example 29 | 0 to 15 | yes | | 6% | 14 | 17.9 | 31 | 1.1 |
| Example 30 | 0 to 15 | yes | | 6% | 14 | 16.1 | 21 | 2.2 |
| Example 31 | 0 to 15 | yes | | 6% | 14 | 15.1 | 12 | 20.0 |
| Example 32 | 0 to 15 | yes | | 6% | 13.4 | 16.1 | 11 | 28 |
| Example 33 | 0 to 15 | yes | | 6% | 13.4 | 16.7 | 13 | 26 |
| Example 34 | 0 to 15 | yes | | 6% | 13.4 | 15.1 | <5 | 29 |
| Example 35 | 0 to 15 | yes | | 6% | 13.8 | 20.6 | 22 | 25 |
| Comparative Example 7 | 0 to 15 | yes | | 6% | 13.6 | 17.9 | 1643 | 34.5 |

Example 36

The aqueous solutions synthesized in Example 8, Example and Example 16 were each subjected to a low-temperature storage test for 10 days using a −10° C. constant temperature bath. As a result, only the solution of Example 8 did not freeze. Based on this result, it was evident that using a combination of sodium hydroxide and potassium hydroxide yielded a greater freezing point depression, resulting in superior product stability at low temperatures.

As shown above, by using the method of the Examples, in which a reaction was induced by adding bromine, under an inert gas atmosphere, to a mixed solution comprising water, an alkali hydroxide and sulfamic acid, and in which the proportion of bromine added was restricted to not more than 25 wt % relative to the total weight of the composition, a one-liquid stabilized hypobromous acid composition which contained substantially no bromate ions, had excellent sterilization performance, exhibited almost no corrosiveness relative to metals, and displayed excellent storage stability was able to be obtained.

Next, the case where a bromine-based oxidizing agent, or a reaction product of a bromine compound and a chlorine-based oxidizing agent, and a sulfamic acid compound were used, and the case where a typical slime inhibitor such as hypochlorous acid, hypobromous acid or chlorosulfamic acid was used were compared in terms of the effect on the RO membrane rejection rate, the effect on the permeate, the oxidizing power, and the sterilization power.

Example 37

Preparation of Compositions

Liquid bromine: 16.9 wt %, sulfamic acid: 10.7 wt %, sodium hydroxide: 12.9 wt %, potassium hydroxide: 3.94%, and water: the balance were mixed together under a nitrogen atmosphere to prepare a composition. The pH of the composition was 14, and the effective halogen concentration (effective equivalent chlorine concentration) was 7.5 wt %. A more detailed description of the preparation method for the composition of Example 37 is presented below.

A 2 liter four-necked flask into which nitrogen gas was injected continuously at a flow rate controlled by a mass flow controller so that the oxygen concentration inside the reaction vessel was maintained at 1% was charged with 1,436 g of water and 361 g of sodium hydroxide, and following mixing, 300 g of sulfamic acid was added and mixed, and with the flask then cooled to maintain the temperature of the reaction solution at 0 to 15° C., 473 g of liquid bromine was added, and 230 g of a 48% solution of potassium hydroxide was then added, thus obtaining the target composition containing 10.7 wt % of sulfamic acid and 16.9 wt % of bromine relative to the total weight of the composition, and having a ratio for the equivalent weight of sulfamic acid relative to the equivalent weight of bromine of 1.04. Measurement of the pH of the prepared solution using the glass electrode method yielded a value of 14. Measurement of the bromine content of the prepared solution using a method in which the bromine was substituted with iodine using potassium iodide, and a redox titration was then performed using sodium thiosulfate revealed a value of 16.9%, which was 100.0% of the theoretical content (16.9%). Further, the oxygen concentration inside the reaction vessel during the bromine reaction was measured using an "Oxygen Monitor JKO-02 LJDII" manufactured by Jikco Ltd. The bromate concentration was less than 5 mg/kg.

Example 38

Sodium bromide: 11 wt %, a 12% aqueous solution of sodium hypochlorite: 50 wt %, sodium sulfamate: 14 wt %, sodium hydroxide: 8 wt %, and water: the balance were mixed together to prepare a composition. The pH of the composition was 14, and the effective halogen concentration (effective equivalent chlorine concentration) was 6 wt %. A more detailed description of the preparation method for the composition of Example 38 is presented below.

A reaction vessel was charged with 17 g of water, 11 g of sodium bromide was added and dissolved by stirring, 50 g of a 12% aqueous solution of sodium hypochlorite was then added and mixed, 14 g of sodium sulfamate was added and dissolved by stirring, and 8 g of sodium hydroxide was then added and dissolved by stirring to obtain the target composition.

Example 39

Each of the components of Example 38 was added separately to water.

Example 40

A composition comprising bromine chloride, sodium sulfamate and sodium hydroxide was used. The pH of the composition was 14, and the effective halogen concentration (effective equivalent chlorine concentration) was 7 wt %.

Comparative Example 8

A 12% aqueous solution of sodium hypochlorite was used.

Comparative Example 9

Sodium bromide: 15 wt % and a 12% aqueous solution of sodium hypochlorite: 42.4 wt % were added separately to water.

Comparative Example 10

A 12% aqueous solution of sodium hypochlorite: 50 wt %, sulfamic acid: 10 wt %, sodium hydroxide: 8 wt %, and water: the balance were mixed together to prepare a composition. The pH of the composition was 14, and the effective halogen concentration (effective equivalent chlorine concentration) was 6 wt %.

[Comparative Tests for Effect on RO Membrane Rejection Rate, Effect on Permeate, and Oxidizing Power]

Under the conditions described below, each of the compositions prepared in Examples 37, 38 and 40 and Comparative Examples 8 and 10, and each of the compositions from Example 39 and Comparative Example 9 was added to the raw water in a reverse osmosis membrane device, and the effect on the RO membrane rejection rate, the effect on the permeate, and the oxidizing power were compared.

(Test Conditions)
  Test device: flat membrane test device
  Separation membrane: polyamide-based polymer reverse osmosis membrane ES20, manufactured by Nitto Denko Corporation
  Operating pressure: 0.75 MPa
  Raw water: Sagamihara well water (pH: 7.2, conductivity: 240 μS/cm)
  Reagent: each of the compositions prepared in Examples 37, 38 and 40 and Comparative Examples 8 and 10, and each of the compositions from Example 39 and Comparative Example 9 was added in sufficient amount to produce an effective halogen concentration (effective equivalent chlorine concentration) of 10 mg/L.

(Evaluation Method)
  Effect on RO membrane rejection rate: the conductivity rejection rate (%) after 30 days operation (100−[permeate conductivity/feed water conductivity]×100)

Effect on permeate: the effective halogen concentration (effective equivalent chlorine concentration, mg/L) within the permeate one hour after addition of the reagent was measured by the DPD method using a residual chlorine measuring instrument (DR-4000, manufactured by Hach Company).
  Oxidizing power: the oxidation-reduction potential (ORP) of the feed water after one hour was measured using an oxidation-reduction potential measuring device (RM-20P ORP meter, manufactured by DKK-TOA Corporation).

[Comparative Test of Sterilization Power]

Under the conditions described below, each of the compositions prepared in Examples 37, 38 and 40 and Comparative Examples 8 and 10, and each of the compositions from Example 39 and Comparative Example 9 was added to a simulated water, and the sterilization power was compared.

(Test Conditions)

Water: a simulated water prepared by adding normal bouillon was added to Sagamihara well water to adjust the number of general bacteria to $10^5$ CFU/ml.

Reagent: the compositions prepared in Examples 37, 38 and 40 and Comparative Examples 8 and 10, and each of the compositions from Example 39 and Comparative Example 9 was added in sufficient amount to produce an effective halogen concentration (effective equivalent chlorine concentration) of 1 mg/L (effective halogen concentration measurement method: measured by the DPD method using a residual chlorine measuring instrument (DR-4000, manufactured by Hach Company)).

(Evaluation Method)

The number of general bacteria 24 hours after the addition of the reagent was measured using a bacterial count measuring kit (Biochecker TTC, manufactured by San-Ai Oil Co., Ltd.).

The test results are shown in Table 3.

TABLE 3

Comparison of RO membrane rejection rate, effective halogen concentration in RO permeate, ORP, and bacterial count

| | RO membrane rejection rate (after 30 days operation) (%) | Effective halogen concentration in RO permeate (mg/L) | ORP (mV) | Bacterial count after 24 hours (CFU/ml) |
|---|---|---|---|---|
| Example 37 | 99 | <0.01 | 650 | $<10^3$ |
| Example 38 | 92 | 0.5 | 620 | $<10^3$ |
| Example 39 | 90 | 1.0 | 660 | $<10^3$ |
| Example 40 | 97 | 0.2 | 630 | $<10^3$ |
| Comparative Example 8 (hypochlorous acid) | 71 | 5.5 | 790 | $<10^3$ |
| Comparative Example 9 (hypobromous acid) | — | 2.0 | 800 | $<10^3$ |
| Comparative Example 10 (chlorosulfamic acid) | 99 | 0.02 | 500 | $10^4$ |

Examples 37 to 40 maintained a high RO membrane rejection rate, exhibited a low effective halogen concentration (effective equivalent chlorine concentration) in the permeate, and had excellent oxidizing power and sterilization power. Among Examples 37 to 40, Example 37 maintained the highest RO membrane rejection rate, and also exhibited the lowest effective halogen concentration (effective equivalent chlorine concentration) in the permeate.

Comparative Example 8 exhibited high oxidizing power and sterilization power, but the RO membrane rejection rate decreased, and the effective halogen concentration (effective equivalent chlorine concentration) in the permeate was also high. Comparative Example 9 exhibited high oxidizing power and sterilization power, but the effective halogen concentration (effective equivalent chlorine concentration) in the permeate was high. In Comparative Example 10, the RO membrane rejection rate underwent almost no reduction, and the effective halogen concentration (effective equivalent chlorine concentration) in the permeate was low, but the oxidizing power was low, and the sterilization power was also low.

In this manner, by incorporating a bromine-based oxidizing agent, or a reaction product of a bromine compound and a chlorine-based oxidizing agent, and a sulfamic acid compound, or alternatively, by incorporating a reaction product of a sulfamic acid compound with a bromine-based oxidizing agent, or a reaction product of a bromine compound and a chlorine-based oxidizing agent, in the feed water supplied to a membrane separation device containing an RO membrane, degradation of the separation membrane and deterioration in the water quality of the treated water was able to be inhibited, and a satisfactory slime inhibitory effect was also able to be obtained.

[Comparative Test of Bromate Ion Concentration in Permeate]

The bromate ion concentration in the permeate was compared for the cases where nitrogen gas purging was either performed or not performed during composition preparation.

Example 41

In a similar manner to Example 37, liquid bromine: 17 wt %, sulfamic acid: 10.7 wt %, sodium hydroxide: 12.9 wt %, potassium hydroxide: 3.95%, and water: the balance were mixed together under a nitrogen atmosphere to prepare a composition. The pH of the composition was 14, the effective halogen concentration (effective equivalent chlorine concentration) was 7.5 wt %, and the bromate concentration was less than 5 mg/kg.

Example 42

Without performing nitrogen purging, liquid bromine: 17 wt %, sulfamic acid: 10.7 wt %, sodium hydroxide: 12.9 wt %, potassium hydroxide: 3.95%, and water: the balance were mixed together under normal atmospheric conditions to prepare a composition. The pH of the composition was 14, the effective halogen concentration (effective equivalent chlorine concentration) was 7.4 wt %, and the bromate concentration was 63 mg/kg.

(Test Conditions)

Test device: flat membrane test device

Separation membrane: polyamide-based polymer reverse osmosis membrane ES20, manufactured by Nitto Denko Corporation Operating pressure: 0.75 MPa Raw water: Sagamihara well water (pH: 7.2, conductivity: 240 μS/cm)

Reagent: the compositions prepared in Examples 41 and 42 were each added in sufficient amount to produce an effective halogen concentration (effective equivalent chlorine concentration) of 50 mg/L.

(Evaluation Method)

The bromate ion concentration in the permeate was measured using an ion chromatography post-column absorbance method.

The test results are shown in Table 4.

TABLE 4

Bromate concentration in feed water and permeate

| | In feed water (μg/L) | In permeate (μg/L) |
|---|---|---|
| Example 41 | <1 | <1 |
| Example 42 | 42 | 1 |

In Example 41, the bromate ion concentration in both the feed water and the permeate was less than 1 μg/L. In Example 42, the bromate ion concentration in both the feed water and the permeate was higher compared with the corresponding value in Example 41.

[Comparative Tests on the Effect of pH of Feed Water Supplied to RO Device on Permeate Volume and Membrane Rejection Rate]

The effects of the pH of the feed water supplied to the RO device on the permeate volume and the membrane rejection rate were investigated.

(Test Conditions)
Test device: flat membrane test device
Separation membrane: polyamide-based polymer reverse osmosis membrane ES20, manufactured by Nitto Denko Corporation
Operating pressure: 0.75 MPa
Raw water: Sagamihara well water (pH: 7.2, conductivity: 240 μS/cm)
Reagent: the composition prepared in Example 1 was added in sufficient amount to produce an effective halogen concentration (effective equivalent chlorine concentration) of 1 mg/L (effective halogen concentration measurement method: measured by the DPD method using a residual chlorine measuring instrument (DR-4000, manufactured by Hach Company)).
RO membrane feed water pH: 4.0 (Example 43-1), 5.0 (Example 43-2), 5.5 (Example 43-3), 6.0 (Example 43-4), 6.5 (Example 43-5), 7.0 (Example 43-6), 7.5 (Example 43-7), 8.0 (Example 43-8), 8.5 (Example 43-9), or 9.0 (Example 43-10)

(Evaluation Method)
Effect on RO membrane rejection rate: the conductivity rejection rate (%) after 120 hours operation (100−[permeate conductivity/feed water conductivity]×100)

Effect on permeate volume: retention rate of permeate volume after 24 hours operation (%, relative to initial value)

The test results are shown in Table 5.

TABLE 5

| | pH of RO membrane permeate | Retention rate of RO membrane permeate volume (after 24 hours operation) (% relative to initial value) | RO membrane rejection rate (after 120 hours operation) (%) |
|---|---|---|---|
| Example 43-1 | 4.0 | 44 | 99 |
| Example 43-2 | 5.0 | 57 | 99 |
| Example 43-3 | 5.5 | 80 | 99 |
| Example 43-4 | 6.0 | 94 | 99 |
| Example 43-5 | 6.5 | 97 | 99 |
| Example 43-6 | 7.0 | 97 | 99 |
| Example 43-7 | 7.5 | 97 | 99 |
| Example 43-8 | 8.0 | 97 | 99 |
| Example 43-9 | 8.5 | 99 | 99 |
| Example 43-10 | 9.0 | 99 | 99 |

In Examples 43-1 to 43-10, no reduction in the rejection rate was observed, indicating that RO membrane degradation was inhibited (the RO membrane rejection rate after 120 hours was 99% or greater). Particularly in Examples 43-3 to 43-10, there was also no significant decrease observed in the permeate volume (the RO membrane permeate volume after 24 hours operation was at least 80% of the initial value). In contrast, in Examples 43-1 and 43-2, although no decrease in the rejection rate was observed, indicating good suppression of RO membrane degradation, the permeate volume decreased.

The invention claimed is:

1. A slime inhibition method for a separation membrane, the method comprising:
    incorporating, in a feed water or a wash water supplied to a membrane separation device containing the separation membrane, a stabilized hypobromous acid composition selected from the group consisting of A), B) or C), wherein A), B) and C) are as defined below:
    A) a stabilized hypobromous acid composition obtained from a method for producing a stabilized hypobromous acid composition, the method comprising:
        inducing a reaction by adding bromine, under an inert gas atmosphere, to a mixed solution comprising water, an alkali hydroxide and sulfamic acid, wherein
    a proportion of bromine added is not more than 25 wt% relative to a total weight of the composition;
    B) a stabilized hypobromous acid composition comprising a reaction product of a bromine-based oxidizing agent and a sulfamic acid compound; and
    C) a stabilized hypobromous acid composition comprising a reaction product of a sulfamic acid compound with a reaction product of a bromine compound and a chlorine-based oxidizing agent; and
    contacting the separation membrane with said stabilized hypobromous acid composition and/or passing said stabilized hypobromous acid composition through the separation membrane, wherein
    the separation membrane is a reverse osmosis membrane composed of a polyamide-based polymer membrane or a nanofiltration membrane composed of a polyamide-based polymer membrane,
    the bromine-based oxidizing agent is bromine or bromine chloride, and
    a ratio of the equivalent weight of the sulfamic acid compound relative to the equivalent weight of the bromine-based oxidizing agent or the reaction product of a bromine compound and a chlorine-based oxidizing agent is 1 or greater.

2. The slime inhibition method for a separation membrane according to claim 1, wherein
    the membrane separation device comprises a reverse osmosis (RO) membrane as the separation membrane, and
    a pH of a feed water supplied to the membrane separation device is 5.5 or higher.

3. The slime inhibition method for a separation membrane according to claim 1, wherein
    a bromate concentration in the stabilized hypobromous acid composition is less than 5 mg/kg.

* * * * *